United States Patent [19]

D'Amico

[11] 4,371,388
[45] Feb. 1, 1983

[54] 3-SUBSTITUTED AMINOALKYL-2-BENZOTHIAZOLINONES AS PLANT GROWTH REGULANTS

[75] Inventor: John J. D'Amico, Olivette, Mo.

[73] Assignee: Monsanto Company, St. Louis, Mo.

[21] Appl. No.: 115,475

[22] Filed: Jan. 25, 1980

[51] Int. Cl.³ .................. A01N 43/78; C07D 277/68
[52] U.S. Cl. ........................................ 71/90; 548/157; 71/88; 71/92; 71/94
[58] Field of Search ................................ 71/90

[56] References Cited

U.S. PATENT DOCUMENTS 3,244,703  4/1966  Yates et al. ............................ 71/90
3,542,538  11/1970  Sung et al. ............................ 71/90
3,993,468  11/1976  D'Amico ............................... 71/90
4,049,419  9/1977  D'Amico ............................... 71/90

OTHER PUBLICATIONS

Sohar, J., Het. Chem., 6, pp. 163–174, (1969).

Primary Examiner—Donald G. Daus
Assistant Examiner—D. B. Springer
Attorney, Agent, or Firm—Patricia A. Coburn; Howard C. Stanley

[57] ABSTRACT

This disclosure relates to 3-substituted aminoalkyl-2-benzothiazolinones which are useful as plant growth regulants. More specifically, this disclosure relates to 3-substituted aminoalkyl-2-benzothiazolinones and compositions containing said compounds and to the use of said compounds and compositions to regulate the growth of leguminous plants such as soybeans.

10 Claims, No Drawings

3-SUBSTITUTED AMINOALKYL-2-BENZOTHIAZOLINONES AS PLANT GROWTH REGULANTS

This invention relates to 3-substituted aminoalkyl-2-benzothiazolinones which are useful as plant growth regulants. More specifically, this invention relates to 3-substituted aminoalkyl-2-benzothiazolinones and compositions containing said compounds and to the use of said compounds and compositions to regulate the growth of leguminous plants.

The compounds of the present invention are represented by the formula

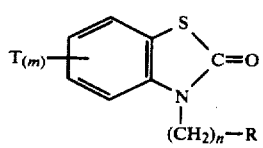
(I)

wherein T is halogen, m is an integer of from 0 to 2, n is an integer of from 1 to 3, and R is a

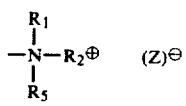

group or a

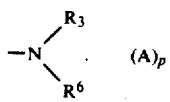

group wherein Z is halogen, p is an integer 0 or 1, A is a strong acid having a pKa in water of 2.5 or less, $R_1$ and $R_2$ are independently lower alkyl, $R_3$ is hydrogen or lower alkyl, $R_5$ is independently selected from the group consisting of lower alkyl, phenyl, a halopyridinyl group and a

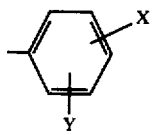

group wherein X is selected from the group consisting of hydrogen, halogen, lower alkyl and trifluoromethyl and Y is lower alkyl or trifluoromethyl, $R_6$ is hydrogen or a group represented by $R_4$, and $R_1$ and $R_5$ together with the nitrogen or $R_3$ and $R_6$ together with the nitrogen can form a cyclic ring selected from the group consisting of piperidyl, morpholino and N'-lower alkyl-piperazinyl.

It is preferred that $R_6$ be selected from the group consisting of a phenyl, a halopyridinyl group and a

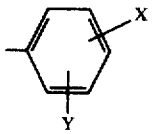

group wherein X is selected from the group consisting of hydrogen, halogen, lower alkyl and trifluoromethyl and Y is lower alkyl or trifluoromethyl. It is more preferred that $R_1$ and $R_5$ together with the nitrogen or $R_3$ and $R_6$ together with the nitrogen can form a cyclic ring selected from the group consisting of piperidyl, morpholino and N'-lower alkyl-piperazinyl.

The term "halo" or "halogen" as used herein is understood to mean fluorine, chlorine, bromine or iodine.

As employed herein, the term "lower alkyl" designates alkyl radicals which have up to four carbon atoms in a straight or branched chain, such as, for example, methyl, ethyl, propyl, isopropyl, butyl, isobutyl, sec-butyl and t-butyl.

Illustrative of the

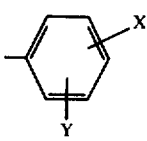

group which $R_5$ and $R_6$ represents are mono-substituted phenyl wherein the substituent is in the ortho, meta or para position, for example, methylphenyl, butylphenyl, trifluoromethylphenyl and the like and di-substituted phenyl wherein the substituents are located in the 2, 3, 4, 5 and 6 positions of the phenyl ring, for example, methylchlorophenyl, diethylphenyl, butyltrifluoromethylphenyl, bromotrifluoromethylphenyl and the like.

As employed herein, the term "halopyridinyl" includes the groups

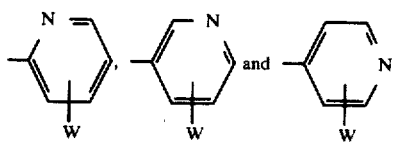

wherein W is halogen.

The acid salts of the compounds of formula (I) are derived from "strong acids" which is understood herein to mean those inorganic and organic acids having a pKa in water of 2.5 or less, and include, for example, hydrohalic acids such as hydrochloric acid, trichloroacetic acid and tri-fluoroacetic acid, oxalic acid, maleic acid and the like. Preferred salts are derived from oxalic acid and the hydrohalic acids, especially hydrochloric acid.

In accordance with the present invention, the compounds of the formula

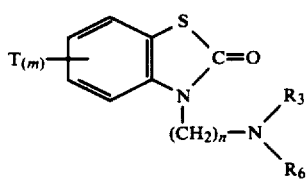 (II)

wherein $R_3$, $R_6$, T, n and m are above-defined may be prepared in accordance with one of the following procedures:

Procedure A: An aqueous solution containing a 2-hydroxybenzothiazole of the formula

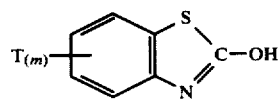 (III)

wherein T and m are above-defined in the presence of a base is treated with a compound of the formula

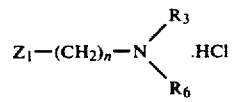 (IV)

wherein $R_3$ and $R_6$ and n are above-defined and $Z_1$ is halogen; at reflux temperatures to produce a compound of formula (II).

The base employed in Procedure A should be capable of forming a salt with the 2-hydroxybenzothiazole of formula (III). Selection of the base is well within the ordinary skill in the art and includes, for example, potassium hydroxide, potassium carbonate, triethylamine, sodium hydroxide and the like.

The ratio of reactants in Procedure A can vary over wide ranges. For best results, for each mole of a compound of formula (III), one employs one mole of a compound of formula (IV) and two moles of a base. For ease of reaction and recovery of product, it is preferred to employ an excess of a compound of formula (III).

Procedure B: A 3-hydroxyalkyl-2-benzothiazolinone of the formula

 (V)

wherein T, m and n are above defined; is treated with a compound of the formula

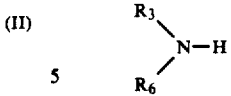 (VI)

wherein $R_3$ and $R_6$ are above defined; in a solvent to produce a compound of formula (II).

Procedure C: A 2-hydroxybenzothiazole of formula (III) is treated with formaldehyde and a compound of formula (VI) in a solvent to produce a compound of formula (II).

Procedures B and C described above may be conducted within a temperature range of 20°-80° C. For ease of reaction and recovery of product, the reflux temperature of the solvent is preferred.

The ratio of reactants can vary over a wide range. In Procedure B, for best results, for each mole of a compound of formula (V), one employs one mole of a compound of formula (VI). For ease of reaction and recovery of product, it is preferred to employ an excess of compound of formula (VI). In Procedure C, for best results, for each mole of a compound of formula (III), one employs one mole of a compound of formula (VI). For ease of reaction and recovery of product, it is preferred to employ an excess of compound of formula (VI).

Due to the reactive nature of the reactants and intermediates, a solvent which will not react with the reactants or products is employed in the processes of Procedures B and C. It is preferred to employ a water-miscible alcohol in which the compounds of formula (II) are soluble. The determination of such solvents is well within the skill of the art and includes, for example, methanol, propanol and the like.

The term "active ingredient" as used herein refers to the novel 3-substituted aminoalkyl-2-benzothiazolines of formula (I).

The following illustrative, non-limiting examples will serve to further demonstrate to those skilled in the art the manner in which specific compounds within the scope of this invention can be prepared. In the examples, all parts are parts by weight unless otherwise expressly stated.

EXAMPLE 1

To a stirred solution containing 30.2 g. (0.2 mol.) of 2-hydroxybenzothiazole and 26.4 g. (0.4 mol.) of 85% potassium hydroxide in 300 ml. of water was added 0.2 mol. of N-(2-chloroethyl)piperidine or N-(2-chloroethyl)morpholine or 2-diethylaminoethyl chloride hydrochloride in one portion. The stirred reaction mixture was heated at reflux for 24 hours. After cooling the reaction mixture to 25° C., 600 ml. of ethyl ether was added to the mixture and the resulting mixture was stirred for 15 minutes at 25°-30° C. The layers were separated and the ether layer was washed with water until neutral to litmus and dried over sodium sulfate. The ether was removed in vacuo at 1-2 mm at a maximum temperature of 80°-90° C. to yield the product. The data are summarized in Table I.

TABLE I

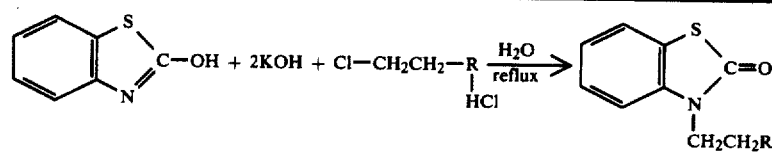

| Compound No. | R | Physical State | b.p. | $n_D^{25}$ | Percent Yield | Elemental Analysis | | | | | | | |
|---|---|---|---|---|---|---|---|---|---|---|---|---|---|
| | | | | | | Carbon | | Hydrogen | | Nitrogen | | Sulfur | |
| | | | | | | Calc'd. | Found | Calc'd. | Found | Calc'd. | Found | Calc'd. | Found |
| 1 | −N⟨piperidine⟩ | dark amber liquid | — | — | 86 | 64.09 | 63.88 | 6.92 | 6.98 | 10.68 | 10.55 | 12.22 | 12.36 |
| 2 | −N⟨morpholine⟩ | very viscous dark amber liquid | — | — | 68 | 59.07 | 59.30 | 6.10 | 6.16 | 10.60 | 10.60 | 12.13 | 12.29 |
| 3 | −N(C₂H₅)₂ | | 150–2° C. @ 0.2 mm Hg | 1.5704 | 75 | 62.37 | 62.09 | 7.25 | 7.30 | 11.19 | 11.02 | 12.81 | 13.00 |

EXAMPLE 2

To a stirred slurry containing 18.1 g. (0.1 mol.) of 3-hydroxymethyl-2-benzothiazoline in an appropriate amount of Solvent A as specified in Table II was added 0.11 ml. of the appropriate amine in one portion. The stirred reaction mixture was heated at reflux and then at 25°–30° C. for a time period specified in Table II. After cooling the reaction mixture to 0° C., an appropriate amount of Solvent B as specified in Table II was added to the mixture and the resulting mixture was stirred for an additional 30 minutes at 0°–10° C. A solid product was collected by filtration and air-dried at 25°–30° C. The data are summarized in Table II.

TABLE II

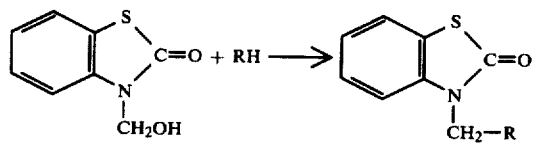

| Compound No. | R | Solvent A | | Reaction Time (hr) | | Solvent B | | m.p. °C. | Percent Yield | Elemental Analysis | | |
|---|---|---|---|---|---|---|---|---|---|---|---|---|
| | | Methanol | Isopropanol | at Reflux Temperature | at 25–30° C. | Heptane | Water | | | Element | Calc'd. | Found |
| 4 | −N(C₂H₅)₂ | 40 ml. | — | 0.5 | 24 | — | — | 53–54(a) | 89 | C | 60.99 | 60.17 |
| | | | | | | | | | | H | 6.82 | 6.44 |
| | | | | | | | | | | N | 11.85 | 11.37 |
| 5 | −N(H)−C₆H₃(CF₃)(Cl) | — | 50 ml. | 1.0 | — | 100 ml. | — | 158–9(b) | 84 | C | 50.22 | 50.33 |
| | | | | | | | | | | H | 2.81 | 2.84 |
| | | | | | | | | | | N | 7.81 | 7.81 |
| | | | | | | | | | | S | 8.94 | 8.94 |
| 6 | −N(H)−C₆H₃(Cl)(CF₃) | — | 50 ml. | 6.0 | 18 | 100 ml. | — | 141–2(b) | 47 | C | 50.22 | 50.87 |
| | | | | | | | | | | H | 2.81 | 3.09 |
| | | | | | | | | | | N | 7.81 | 7.34 |
| | | | | | | | | | | S | 8.94 | 8.70 |
| 7 | −N⟨piperidine⟩ | — | 40 ml. | 1.0 | — | — | 25 ml. | 93–4(c) | 81 | C | 62.87 | 62.68 |
| | | | | | | | | | | H | 6.49 | 6.51 |
| | | | | | | | | | | N | 11.28 | 11.25 |
| | | | | | | | | | | S | 12.91 | 12.84 |

TABLE II-continued

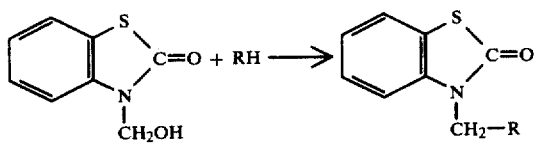

| Compound No. | R | Solvent A Methanol | Solvent A Isopropanol | Reaction Time (hr) at Reflux Temperature | at 25-30° C. | Solvent B Heptane | Water | m.p. °C. | Percent Yield | Elemental Analysis Element | Calc'd | Found |
|---|---|---|---|---|---|---|---|---|---|---|---|---|
| 8 | H-N-(3,5-bis-CF₃-phenyl) | — | 50 ml. | 6.0 | 18 | — | 800 ml. | 139-40[d] | 51 | C H N S | 48.98 2.57 7.14 8.17 | 48.92 2.61 7.11 8.33 |
| 9 | H-N-(3-CF₃-phenyl) | 20 | — | 0.5 | — | — | — | 121-2[d] | 96 | C H N S | 55.55 3.42 8.64 9.89 | 55.62 3.42 8.63 9.91 |
| 10 | H-N-(5-Cl-pyridin-2-yl) | — | 100 | 1.0 | — | 50 ml. | — | 179-80[e] | 38 | C H N S | 53.52 3.45 14.40 10.99 | 53.50 3.46 14.41 10.92 |

[a] Methanol removed in vacuo (1-2 mm Hg) at a temperature of 80-90° C.
[b] Recrystallized from isopropyl alcohol
[c] Recrystallized from heptane
[d] Recrystallized from heptane-isopropyl alcohol
[e] Recrystallized from toluene

EXAMPLE 3

A stirred slurry containing 0.1 mol. of 2-hydroxybenzothiazole or 6-bromo-2-hydroxybenzothiazole and 16 ml. of 37% aqueous formaldehyde in an appropriate amount of Solvent A as specified in Table III, was heated at reflux for 30 minutes. After cooling the slurry to 25° C., 0.11 mol. of the appropriate amine was added in one portion to the slurry. The reaction mixture was stirred at reflux and/or at 25°-30° C. for a time period as specified in Table III. For Compound Nos. 11-14, after cooling the reaction mixture to 0° C., an appropriate amount of Solvent B was added and the resulting mixture was stirred at 0°-10° C. for one hour. A solid product was collected by filtration and air-dried at 25°-30° C. For Compound 15, after the reaction mixture was cooled to 25°-30° C., 300 ml. of ethyl ether was added to the mixture and the resulting mixture was stirred at 25°-30° C. for 15 minutes. The layers were separated and the ether layer was washed with water until neutral to litmus and then dried over sodium sulfate. The ether was removed in vacuo at 1-2 mm Hg at a maximum temperature of 80°-90° C. to yield a viscous amber liquid. The data for Compound Nos. 11-15 are summarized in Table III.

TABLE III

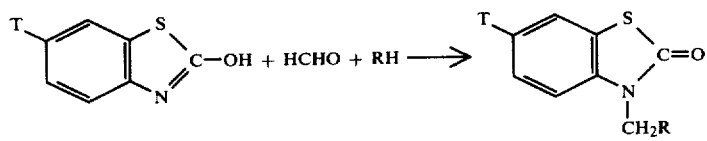

| Compound No. | R | T | Solvent A Methanol | Solvent A Isopropanol | Reaction Time (hr.) Reflux | Reaction Time (hr.) 25-30° C. | Solvent B Solvent | Solvent B ml. | m.p. °C. | Percent Yield | Element | Calc'd | Found |
|---|---|---|---|---|---|---|---|---|---|---|---|---|---|
| 11 | -N(morpholine) | -H | 20 ml. | — | 0.5 | — | Water | 50 | 86-7 | 96 | C H N S | 57.58 5.64 11.19 12.81 | 57.61 5.67 11.21 12.83 |
| 12 | H-N-(2,6-diethylphenyl) | -H | — | 20 ml. | 24 | — | Heptane Isopropanol | 25 37 | 184-5[a] | 78 | N S | 8.97 10.26 | 8.68 10.00 |

TABLE III-continued

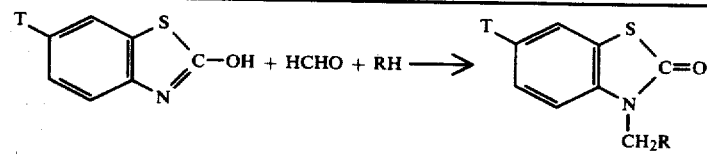

| Compound No. | R | T | Solvent A Methanol | Solvent A Isopropanol | Reaction Time (hr.) Reflux | Reaction Time (hr.) 25-30° C. | Solvent B Solvent | Solvent B ml. | m.p. °C. | Percent Yield | Element | Elemental Analysis Calc'd. | Elemental Analysis Found |
|---|---|---|---|---|---|---|---|---|---|---|---|---|---|
| 13 | −N(piperazinyl)−CH$_3$ | −Br | 40 ml. | — | 1 | 24 | Methanol | 25 | 140–1[b] | 93 | C<br>H<br>N<br>S | 45.62<br>4.71<br>12.28<br>9.37 | 45.68<br>4.76<br>12.24<br>9.38 |
| 14 | −NH−C$_6$H$_5$ | −H | — | 20 ml. | 1 | — | Heptane | 50 | 163–4[c] | 96 | C<br>H<br>N<br>S | 65.60<br>4.72<br>10.93<br>12.51 | 65.58<br>4.75<br>10.90<br>12.51 |
| 15 | −N(CH$_3$)$_2$ | −H | 20 ml. | — | — | 48 | Ethyl Ether | 300 | [d] | 94 | C<br>H<br>N<br>S | 57.67<br>5.81<br>13.45<br>15.39 | 57.03<br>5.57<br>13.63<br>15.77 |

[a] Recrystallized from toluene
[b] Recrystallized from isopropanol
[c] Recrystallized from ethyl acetate
[d] Viscous amber liquid

EXAMPLE 4

To a stirred solution containing 105.9 g. (0.7 mol.) of 2-hydroxybenzothiazole and 102.1 g. (1.5 mol.) of sodium ethoxide in 900 ml. of ethyl alcohol was added 81.2 g. (0.7 mol.) of 2-aminoethyl chloride hydrochloride in one portion. The stirred reaction mixture was heated at reflux for 5 hours and then at 25°–30° C. for 18 hours. The reaction mixture was filtered to remove any sodium chloride. The ethyl alcohol was removed in vacuo at 1-2 mm at a maximum temperature of 80°–90° C. to yield 3-aminoethyl-2-benzothiazolinone (88% yield) (Compound 16) as a viscous liquid having the following analysis:

Calculated: C, 55.65; H, 5.19; S, 16.51. Found: C, 54.96; H, 4.96; S, 16.34.

EXAMPLE 5

To a stirred solution containing 105.9 g. (0.7 mol.) of 2-hydroxybenzothiazole and 92.4 g. (1.4 mol.) of 85% potassium hydroxide in 700 ml. of water was added 115.3 g. (0.7 mol.) of 96% 3-dimethylaminopropyl chloride hydrochloride in one portion. The stirred reaction mixture was heated at reflux for 24 hours and then cooled to 25° C. To the cooled reaction mixture was added 400 g. of sodium chloride and 200 ml. of chloroform and the resulting mixture was stirred for 30 minutes. The layers were separated and the chloroform layer was dried over sodium sulfate. The chloroform was removed in vacuo at 1-2 mm Hg at a maximum temperature of 80°–90° C., to yield 3-dimethylaminopropyl-2-benzothiazolinone (65% yield) (Compound 17) as a viscous dark amber liquid having the following analysis:

Calculated: S, 13.57. Found: S, 14.14.

EXAMPLE 6

To a stirred solution containing 75.6 g. (0.5 mol.) of 2-hydroxybenzothiazole and 74.9 g. (1.1 mol.) of sodium ethoxide in 900 ml. of ethyl alcohol was added 73.5 g. (0.5 mol.) of 2-dimethylaminoethyl chloride hydrochloride in one portion. The stirred reaction mixture was heated at reflux for four hours and then at 25°–30° C. for 18 hours. The reaction mixture was filtered to remove any sodium chloride. The reaction mixture was concentrated in vacuo at 10–12 mm Hg at a maximum temperature of 80°–90° C. to yield a viscous residue. The residue was extracted with 500 ml. of ethyl ether for 1 hour and the resulting extract was filtered to remove any impurity. The ether was removed in vacuo at 1-2 mm at a maximum temperature of 80°–90° C. to yield a residue. The residue was distilled in vacuo to yield 3-dimethylaminoethyl-2-benzothiazolinone (69% yield) (Compound 18) as an oil having a boiling point of 154°–160° C. at 0.2 mm Hg (nD$^{25}$=1.5889) and the following analysis:

Calculated: N, 12.60; S, 14.42. Found: N, 12.10; S, 14.23.

The quarternary salt compounds of the formula

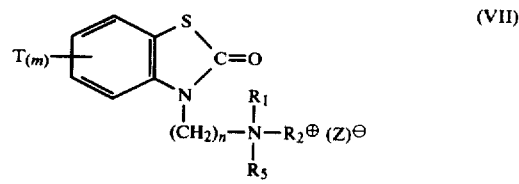

(VII)

can be prepared by treating a compound of the formula

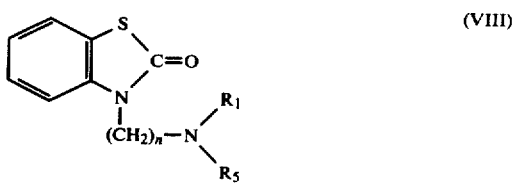

(VIII)

wherein $R_1$, $R_5$, T, m and n are above defined; with an alkyl halide of the formula $$R_2—Z \quad \text{(IX)}$$

wherein $R_2$ and Z are above defined; in the presence of a solvent in which the quarternary salts of formula (VII) are insoluble.

EXAMPLE 7

To a stirred solution containing 0.1 mol. of the appropriate 3-substituted aminoalkyl-2-benzothiazolinone in 150 ml. of ethyl ether was added 28.2 g. (0.2 mol.) of methyl iodide in one portion. After stirring the reaction mixture for 24 hours at 25°–30° C., a solid product was collected by filtration and air-dried at 25°–30° C. The data are summarized in Table IV.

yield) (Compound 22) having a melting point of 227°–228° C. and the following analysis:

Calculated: C, 56.27; H, 6.41; N, 9.37; Cl, 11.86; S, 10.73. Found: C, 56.18; H, 6.43; N, 9.37; Cl, 11.81; S, 10.80.

Compounds of the formula I above have been found to produce a variety of plant growth regulatory responses when applied to leguminous crop plants, for example, soybean (Glycine max). The terms "plant growth regulant effect," "plant growth regulation" or words to that effect, are used in this specification and in the claims to mean the causation by the chemicals of the present invention, of a variety of plant responses which achieve a promotion, inhibition or modification of any plant physiological or morphological process. It should

TABLE IV

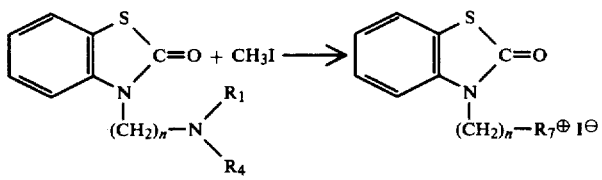

| Compound No. | $R_7$ | n | m.p. °C. | % Yield | Elemental Analysis | | | | | | | |
|---|---|---|---|---|---|---|---|---|---|---|---|---|
| | | | | | Carbon | | Hydrogen | | Sulfur | | Nitrogen | |
| | | | | | Calc'd. | Found | Calc'd. | Found | Calc'd. | Found | Calc'd. | Found |
| 19 | $\begin{array}{c}CH_3\\|\\-N-CH_3\\|\\CH_3\end{array}$ | 2 | 288–290 | 41 | — | — | — | — | 8.80 | 8.82 | 7.69 | 7.92 |
| 20 | $\begin{array}{c}CH_3\\|\\-N-CH_3\\|\\CH_3\end{array}$ | 1 | 114–116 | 57 | 37.73 | 38.38 | 4.32 | 4.40 | 9.16 | 9.04 | 8.00 | 7.68 |
| 21 | $-N\underset{CH_3}{\overset{\frown}{\diagdown}}$ | 2 | 238–240 | 72 | 44.56 | 45.10 | 5.24 | 5.19 | 7.93 | 8.18 | 6.93 | 6.84 |

The strong acid salt compounds of the formula

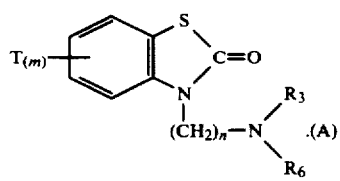

(X)

wherein $R_3$, $R_6$, A, T, n, and m are above defined; can be prepared by treating a compound of formula (II) with a strong acid in the presence of a solvent.

EXAMPLE 8

Anhydrous hydrogen chloride gas was bubbled through a stirred solution containing 28 g. (0.106 mol.) of 3-(2-piperidinoethyl)-2-benzothiazoline in 400 ml. of ethyl ether for 30 minutes at 0°–10° C. After the addition of the hydrogen chloride gas, the reaction mixture was stirred for one hour at 0°–10° C. and then filtered to yield a solid which was air-dried at 50° C. to yield 3-(2-piperidinoethyl)-2-benzothiazoline hydrochloride (94% additionally be recognized that various plant responses may also result from a combination or sequence of both physiological and morphological factors.

The plant growth regulant effects which may be produced in leguminous plants using the method of the present invention are probably most readily observable as changes in the size, shape, color or texture of the treated plant or any of its parts. Similarly, changes in the quantity of the plant fruit or flowers are also quite apparent from visual inspection. The above changes may be characterized as an acceleration or retardation of plant growth, stature reduction, leaf or canopy alteration, increased branching, tillering, terminal inhibition, increased flowering or fruit set, increased root growth, axillary bud development or inhibition, delayed budding, defoliation, desiccation, delayed senescence, prolonged dormancy, increased cold hardiness, delayed or accelerated ripening, and the like.

It is to be understood that each response may occur in conjunction with other responses, but may occur separately. For example, depending upon various factors realized by those skilled in the art to effect activity, the data illustrated below demonstrates that the compounds of the present invention sometimes alter the leaf morphology even though the plants are not reduced in stature.

Alteration of the leaf morphology of leguminous plants is important because leguminous plants have canopies that effectively inhibit sunlight from reaching the lower leaves. For example, only about 50% of a soybean plant's leaves intercept light for photosynthesis. Approximately 85% of the light is absorbed by the outer layer of leaves. Many researchers feel that by altering the morphology of the leaves such that the canopy is altered, light may fall more deeply into the canopy, and yields could be increased. Weber, in "Field Crop Abstracts," Volume 21, No. 4, pages 313–317, states that "greater light penetration, resulting in greater amount of the [soybean] plant canopy having a light intensity above 150 f.c., generally led to higher seed yields." Johnson et al., in "Crop Science," Volume 9, pages 577–581, states that "adding light increased the yields of bottom, middle and top canopy positions of [soybean] plants 30, 20 and 2%, respectively." Thus, it would be highly beneficial if a method was found whereby the leaves of such plants could be altered such that a greater number of leaves could be illuminated.

Although many of the above modifications are per se desirable, it is most often the ultimate effect of such modifications on the economic factor that is of primary significance. For example, reducing the physical size of each plant in a field permits the growing of more plants per unit area and leads to more efficient use of crop land. Many plants of reduced stature are more tolerant of drought and cold temperatures and are more resistant to pest infestations and to lodging. Reduction in the maturation rate on portions of a crop permits an extended harvest period at peak yield and more efficient use of subsequent crop processing equipment. Suppression of vegetative growth at the appropriate stage of the plant's development may result in increased energy available for utilization in reproductive development so that, for example, more fruit or larger fruit is formed.

It is to be understood that the regulation of desirable crop plants in accordance with the instant invention does not include the total inhibition or the killing of such plants. Although phytotoxic amounts of the materials disclosed herein might be employed to exert a herbicidal (killing) action, it is contemplated here to employ only plant regulating amounts of such materials in order to modify the normal sequential development of the treated plant to agricultural maturity. The application of a plant regulating amount may be applied to plants in sequence at various stages of the plants' development to obtain various desirable responses. As may be expected, and as is apparent to those skilled in the art, such plant regulating amounts will vary, not only with the material selected, but also with the modifying effect desired, the species of plant and its stage of development, the plant growth medium and whether a permanent or transitory effect is sought.

In accordance with this invention it has been found that desirable modification of leguminous crop plants is achieved by applying the above-described plant regulants to the "plant" or plant "habitat." The term "plant" is understood herein to include the seeds, emerging seedlings, roots, stems, leaves, flowers, fruits or other plant parts. The term "habitat" is understood herein to mean the environment of the plant such as the plant growing medium, e.g., the soil.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. The plant growth composition may be applied to the plant growth medium if desired.

Compositions of this invention generally contain from about 5 to 95 parts active ingredient, about 1 to 50 parts surface-active agent and about 5 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.056 to about 11.2 kilograms per hectare. Preferred are foliar applications of from 0.056 to 5.6 kilograms of the active ingredient per hectare. In application of the soil habitat of germinant seeds, emerging seedlings and established vegetation for the regulation of plant growth, the active ingredients are applied in amounts of from 0.112 to about 11.2 kilograms per hectare or more. The application to the soil of from 0.112 to about 5.6 kilograms of active ingredient per hectare is preferred. Foliar application to plants beginning to blossom are preferred over other types of applications.

In accordance with the practice of the invention, several plant growth regulating compositions were formulated utilizing several of the 3-substitutedaminoalkyl-2-benzothiazolinones as the active ingredient. The compositions were formulated so that they could be applied at a rate the equivalent of 200 gallons per acre (306 liters per hectare). The formulation of the composition for other rates of application is well within the skill of the art.

Several of the 3-substituted-aminoalkyl-2-benzothiazolinone active compounds exhibited unexpected plant growth regulating properties when tested employing the procedure set forth in Example 9.

EXAMPLE 9

A number of soybean plants, variety Williams, are grown from seeds in plastic pots in the greenhouse for a period of one week at which time the plants are thinned to one plant per pot. When the second trifoliate leaf (three weeks) was fully expanded, the plants were treated with a solution of the active ingredient in acetone and water. Aqueous Tween 20 is used as a surfactant.

When the fifth trifoliate leaf (four to five weeks) was fully expanded, the treated plants were compared with the non-treated control plants and the observations recorded.

Table V below summarizes the results and observations made in accordance with the above procedure.

TABLE V

| Compound No. | RATE kg/ha | % Dry Weight* | Response |
|---|---|---|---|
| 1 | 0.112 | 71 | No response noted |
|  | 0.56 | 91 | Leaf alteration (new growth) |
|  | 2.80 | 86 | Leaf distortion; leaf alteration (new growth); slight leaf burn |
| 3 | 0.112 | 76 | Leaf alteration (new growth) |
|  | 0.56 | 82 | Leaf alteration (new growth) |
|  | 2.80 | 81 | Leaf distortion; leaf inhibition; altered canopy; leaf alteration (new growth); slight leaf burn |
| 4 | 0.112 | 76 | Leaf alteration (new growth) |
|  | 0.56 | 78 | Altered canopy; leaf alteration (new growth) |
|  | 2.80 | 67 | Leaf inhibition; altered canopy; inhibition of apical development; stature reduction; leaf alteration (new growth) |
| 5 | 0.112 | 96 | No response noted |
|  | 0.56 | 92 | Leaf alteration (new growth) |
|  | 2.80 | 88 | Leaf inhibition; altered canopy; stature reduction; leaf alteration (new growth) |
| 7 | 0.112 | 92 | No response noted |
|  | 0.56 | 84 | No response noted |
|  | 2.80 | 79 | Leaf distortion; leaf alteration (new growth); slight leaf burn |
| 10 | 0.112 | 101 | No response noted |
|  | 0.56 | 68 | No response noted |
|  | 2.80 | 85 | Leaf alteration (new growth) |
| 11 | 0.112 | 101 | No response noted |
|  | 0.112 | 111 | No response noted |
|  | 0.56 | 102 | No response noted |

TABLE V-continued

| Compound No. | RATE kg/ha | % Dry Weight* | Response |
|---|---|---|---|
|  | 0.56 | 101 | No response noted |
|  | 2.80 | 68 | Leaf distortion; leaf alteration (new growth); slight leaf burn |
|  | 2.80 | 125 | Leaf distortion; leaf alteration; altered canopy; leaf alteration (new growth); slight leaf burn |
| 14 | 0.112 | 84 | No response noted |
|  | 0.56 | 78 | No response noted |
|  | 2.80 | 79 | Leaf distortion; slight leaf burn |
| 17 | 0.112 | 102 | No response noted |
|  | 0.56 | 85 | No response noted |
|  | 2.80 | 85 | Leaf alteration (new growth); slight leaf burn |
| 20 | 0.112 | 84 | No response noted |
|  | 0.56 | 84 | No response noted |
|  | 2.80 | 90 | Leaf alteration (new growth); slight leaf burn |

*Calculated as percent of control

The following illustrative non-limiting examples will serve to further demonstrate to those skilled in the art the manner in which the compounds of formula (I) can be formulated. In the examples, all parts are parts by weight.

EXAMPLE 10

Wettable Powders (a)

50 Parts of Compound No. 20, 3 parts sodium lignosulfonate, 1 part sodium N-methyl-N-oleyl-taurate and 46 parts kaolinite clay are thoroughly blended, preground by one pass through a hammer mill and then ground using an air mill to produce a wettable powder having an excellent capacity for forming suspensions. By diluting these powders with water, it is possible to obtain suspensions of any desired concentration.

(b)

75 Parts of Compound No. 5, 1.25 parts sodium dioctyl sulfosuccinate, 2.75 parts of calcium lignosulfonate and 21 parts of amorphous silica are thoroughly blended and then ground by passing several times through a hammer mill fitted with a fine screen to produce a wettable powder having an excellent capacity for forming suspensions. By diluting these powders with water, it is possible to obtain suspensions of any desired concentration.

(c)

10 parts of Compound No. 10, 3 parts sodium lignosulfonate, 1 part sodium N-methyl-N-oleyl-taurate, 47 parts kaolinite clay and 40 parts diatomaceous earth are thoroughly blended, pre-ground by one pass through a hammer mill and then ground using an air mill to produce a wettable powder having an excellent capacity for forming suspensions. By diluting these powders with water, it is possible to obtain suspensions of any desired concentration.

EXAMPLE 11

Liquid Concentrates (a)

10 Parts of Compound No. 4, 0.5 parts of polyoxyethylene and 0.5 parts methyl violet are dissolved in 89 parts of dimethyl formamide to produce a liquid concentrate.

(b)

50 Parts of Compound No. 3 and 2 parts of nonylphenyl ether are dissolved in 48 parts of N-methylpyrrolidone to produce a liquid concentrate.

(c)

5 Parts of Compound No. 5, 20.0 parts of ethoxylated castor oil and 0.5 parts Rhodamine B are dissolved in 74.5 parts of dimethyl sulfoxide to produce a liquid concentrate.

(d)

95 Parts of Compound No. 4 are dissolved in 5 parts of dimethyl sulfoxide to produce a liquid concentrate.

EXAMPLE 12

Dust Formulations (a)

1 Part of Compound No. 4 and 99 parts of diatomaceous earth are blended and then passed through a hammer mill and subsequently seived through a 60 mesh screen to produce a dust formulation.

(b)

30 Parts of Compound No. 11, 1 part of ethylene glycol and 69 parts of bentonite are blended and then passed through a hammer mill and subsequently sieved through a 60 mesh screen to produce a dust formulation.

(c)

20 Parts of Compound No. 18, 5 parts of diethylene glycol and 75 parts of talc are blended and then passed through a hammer mill and subsequently seived through a 60 mesh screen to produce a dust formulation.

EXAMPLE 13

Emulsifiable Concentrates (a)

13 Parts of Compound No. 3, 4 parts of an emulsifier blend (calcium dodecyl sulfonate/alkylarylpolyether alcohol blend) and 83 parts xylene are blended in a stirred vessel to produce an emulsifiable concentrate which may be diluted with water to give an emulsion in the desired concentration.

(b)

44 Parts of Compound No. 4, 10 parts of an emulsifier blend (calcium dodecyl sulfonate/alkylarylpolyether alcohol blend) and 46 parts of monochlorobenzene are blended in a stirred vessel with heat being applied to increase the solubility rate of Compound No. 4 to produce an emulsifiable concentrate which may be diluted with water to give an emulsion in the desired concentration.

EXAMPLE 14

Water-Soluble Powders (a)

10 Parts of Compound No. 20, 2 parts of sodium dioctyl sulfosuccinate, 5 parts of silica aerogel, 0.1 parts methyl violet base and 82.9 parts of sodium bicarbonate are blended and then ground to pass through a 30 mesh seive to produce a water-soluble powder which can be diluted with water to yield the desired concentration.

(b)

90 Parts of Compound No. 18 and 10 parts of diammonium phosphate are blended and then ground to pass through a 30 mesh seive to produce a water-soluble powder which can be diluted with water to yield the desired concentration.

EXAMPLE 15

Flowable Formulation (a)

25 Parts of Compound No. 20, 0.3 parts of methyl cellulose, 1.5 parts by weight of silica aerogel, 3.5 parts by weight of sodium lignosulfonate, 2.0 parts by weight of sodium N-methyl-N-oleyl-taurate and 66.7 parts of water are blended and then ground in a sand mill until a flowable formulation having a particle size less than 8–12 microns is obtained. The flowable formulation can be diluted with water to yield the desired concentration.

(b)

45 Parts of Compound No. 22, 0.3 parts of methyl cellulose, 1.5 parts of silica aerogel, 3.5 parts of sodium lignosulfonate, 2.0 parts of sodium N-methyl-N-oleyl-taurate and 47.3 parts of water are blended and then ground in a sand mill until a flowable formulation having a particle size less than 8–12 microns is obtained. The flowable formulation can be diluted with water to yield the desired concentration.

EXAMPLE 16

Granular Formulations (a)

1 Part of Compound No. 3, 5 parts of ethylene glycol and 0.1 parts of methylene blue are sprayed into 93.9 parts of pyrophyllite having a mesh size of 20–40 mesh in a mixer to produce a granular formulation.

(b)

20 Parts of Compound No. 4 is melted and then sprayed onto 80 parts of kaolinite clay having a mesh size of 24–48 in a mixer to produce a granular formulation.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A plant growth regulating composition comprising an inert adjuvant and an effective plant growth regulating amount of a compound of the formula

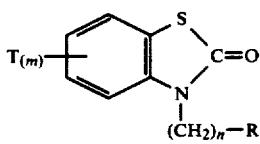

wherein T is halogen, m is an integer of from 0 to 2, n is an integer of from 1 to 3, and R is a

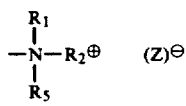

group or a

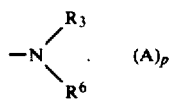

group wherein Z is halogen, p is an integer 0 or 1, A is a strong acid having a pKa in water of 2.5 or less, $R_1$ and $R_2$ are independently lower alkyl, $R_3$ is hydrogen or lower alkyl, $R_5$ is independently selected from the group consisting of lower alkyl, phenyl, a halopyridinyl group and a

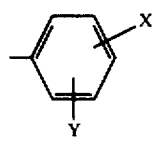

group wherein X is selected from the group consisting of hydrogen, halogen, lower alkyl and trifluoromethyl and y is lower alkyl or trifluoromethyl, $R_6$ is hydrogen or a group represented by $R_5$ and $R_1$ and $R_5$ together with the nitrogen or $R_3$ and $R_6$ together with the nitrogen can form a cyclic ring selected from the group consisting of piperidyl, morpholino and N'-lower alkyl-piperazinyl.

2. A composition according to claim 1 wherein R is a

group.

3. A composition according to claim 2 wherein $R_6$ is selected from the group consisting of a

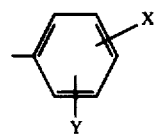

group wherein X is selected from the group consisting of hydrogen, halogen and trifluoromethyl and Y is trifluoromethyl.

4. A composition according to claim 3 wherein $R_3$ is hydrogen.

5. A composition according to claim 4 wherein the compound is 3-(3-trifluoromethyl-4-chloro)-phenylaminoethyl-2-benzothiazolinone.

6. A method of regulating the natural growth and development of leguminous plants which comprises applying to said leguminous plants or their habitat an effective plant growth regulating amount of a compound of the formula

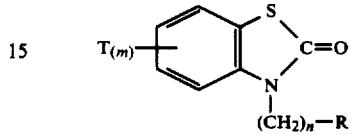

wherein T is halogen, m is an integer of from 0 to 2, n is an integer of from 1 to 3, and R is a

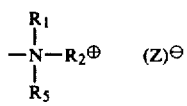

group or a

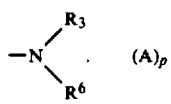

group wherein Z is halogen, p is an integer 0 or 1, A is a strong acid having a pKa in water of 2.5 or less, $R_1$ and $R_2$ are independently lower alkyl, $R_3$ is hydrogen or lower alkyl, $R_5$ is independently selected from the group consisting of lower alkyl, phenyl, a halopyridinyl group and a

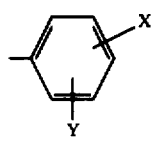

group wherein X is selected from the group consisting of hydrogen, halogen, lower alkyl and trifluoromethyl and Y is lower alkyl or trifluoromethyl, $R_6$ is hydrogen or a group represented by $R_4$ and $R_1$ and $R_5$ together with the nitrogen or $R_3$ and $R_6$ together with the nitrogen can form a cyclic ring selected from the group consisting of piperidyl, morpholino and N'-lower alkyl-piperazinyl.

7. A method according to claim 6 wherein R is a

group.

8. A method according to claim 7 wherein $R_6$ is selected from the group consisting of a

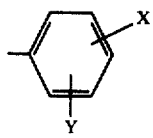
group wherein X is selected from the group consisting of hydrogen, halogen and trifluoromethyl and Y is trifluoromethyl.
9. A method according to claim 8 wherein $R_3$ is hydrogen.
10. A method according to claim 9 wherein the compound is 3-(3-trifluoromethyl-4-chloro)phenylaminoethyl-2-benzothiazolinone.
* * * * *